United States Patent [19]

Rutledge

[11] Patent Number: 4,844,307

[45] Date of Patent: Jul. 4, 1989

[54] OFF ROAD RESCUE BACK PACK

[76] Inventor: Violet M. Rutledge, 37709 Agness-Illahe Rd., Agness, Oreg. 97496

[21] Appl. No.: 143,457

[22] Filed: Apr. 1, 1988

[51] Int. Cl.$^4$ .......................... A45F 3/08; B65D 69/00
[52] U.S. Cl. .................................... 224/211; 224/213; 224/237; 206/570
[58] Field of Search ................ 206/570; 224/211, 237, 224/213

[56] References Cited

U.S. PATENT DOCUMENTS 4,169,550 10/1979 Williams .............................. 206/570
4,449,655 5/1984 Germe ................................. 224/211

Primary Examiner—Henry J. Recla
Assistant Examiner—Robert Fetsuga

[57] ABSTRACT

A back pack with compartments protect and separate emergency medical equipment while maintaining ease of accessibility. The bag adjusts to most standard metal back pack frames for greater stabilization, equipment protection, and personal comfort when hiking extended distances. The bag has no external pockets as in narrow access routes such as brushy type terrain the pockets tend to hook on brances or limbs placing the bearer in danger of injury due to loss of footing or balance.

1 Claim, 3 Drawing Sheets

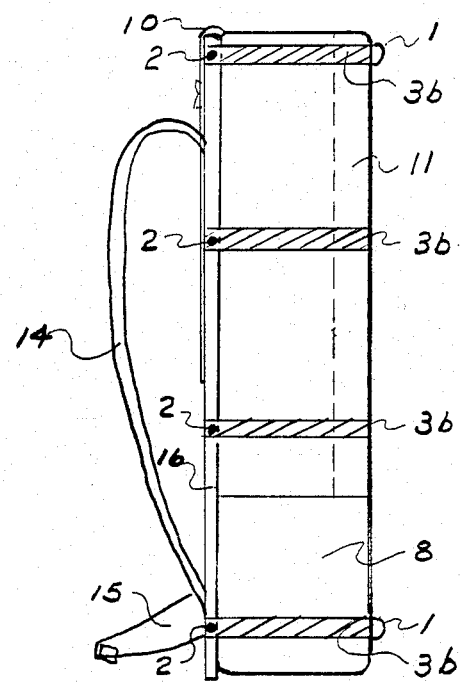
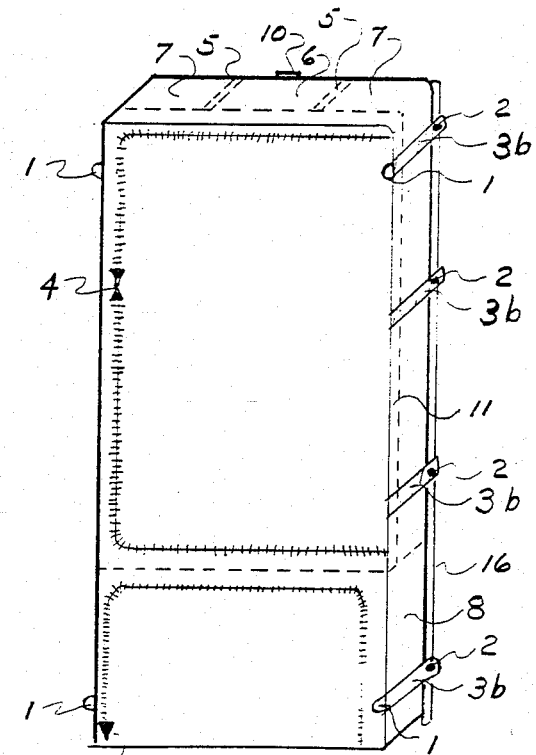
FIG 1
FIG 2

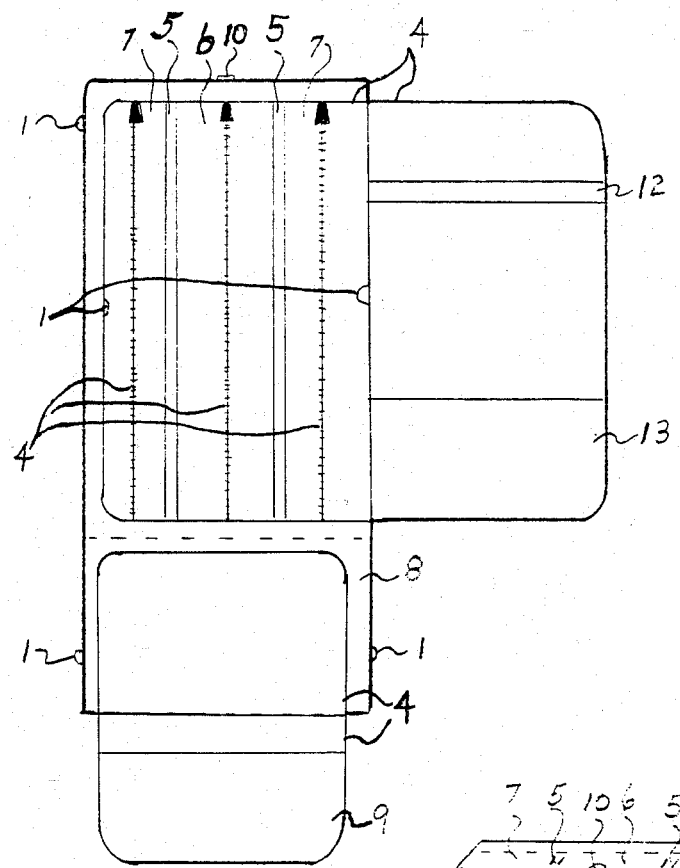
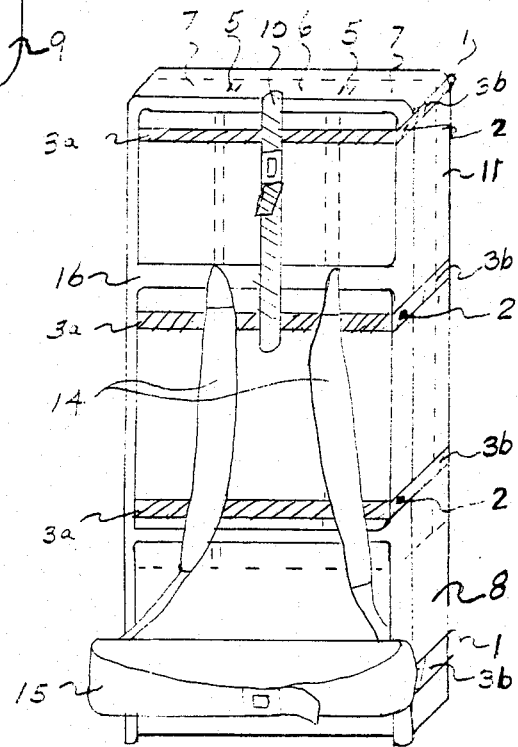
Fig 3
Fig 4

OFF ROAD RESCUE BACK PACK

BACKGROUND OF THE INVENTION

1. FIELD OF THE INVENTION

The standard back packs for camping and hiking do not accommodate well to medical supplies. In the rural or remote setting it is necessary for fewer personnel to respond with all needed medical equipment and supplies to begin the initial stabilization.

2. BACKGROUND ART

With the increase of people in remote areas (over one hour transport time to a hospital) it is necsssary to have all needed emergency equipment upon arrival at the scene of an accident or illness utilizing fewer personnel. Unlike U.S. Pat. No. 4,169,550 issued to Paul K. Williams, small volunteer non-tax supported medical units cannot afford a separate medical kit for each type of emergency. The Off Road Rescue Back Pack equipment and supplies are accessible with the pack either in an upright position or laying flat. Any standard bungi cord, rope, etc., can be used to secure the pack in a vehicle, boat, or aircraft.

The compartment sizes and arrangement in the pack allow the medical supplies and equipment to remain in their original packing to protect against contamination while being cushioned and protected from breakage utilizing other medical equipment and supplies such as trauma dressings and C collars. The pack accommocates a "D" size oxygen cylinder in an upright position with access for use while in the pack. The concept of using medical supplies to protect and cushion medical equipment decreases the need for padding in the pack which eliminates excessive weight and bulk in the pack.

SUMMARY OF THE INVENTION

The bag is primarily designed for but not limited to medical equipment and supplies. When constructed with a water resistant material and sewn seams are treated with a water resistant solution, the bag protects the contents from moisture as well as organizing equipment and supplies for ease of transport to remote areas.

DESCRIPTION OF THE DRAWINGS

FIG. 1 is the side view also showing placement of side and top securing straps.

FIG. 2 is the front view in the closed position. With the exterior upper zipper (4) partially in the open position oxygen access is available while remaining in the bag.

FIG. 3 is the view with both main compartments in the open position.

FIG. 4 is the back view showing placement of back and side support webbing (3 and 10).

DESCRIPTION OF THE PREFERRED EMBODIMENTS

Figure 5:
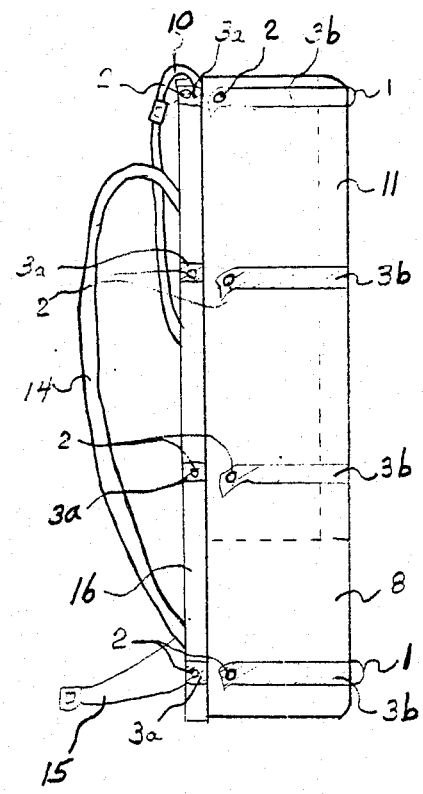

In reference to the drawings of FIGS. 1 through 4 of the back pack bag 1 refers to the "D" rings for rope lowering or raising; 2 refers to the grommets for ring and pin combo securing bag to the metal frame; 3 denotes placement of the side and back web strapping; 4 refers to the placement of zippers and/or Velcro straps.

The two compartments 5 are open $\frac{1}{2}$" by 24" by 6" for placement of soft items such as C collars, air mattress, and soft bulky trauma dressings to cusion the oxygen compartment 6 which is 6" by 5" by 24". The two outside compartments 7 are $4\frac{1}{2}$" by 6" by 24", which contain such items as flashlight, air splints, one-way-valve mask, bag mask, and but not limited to additional trauma dressings. Compartment numbered 8 is 9" by 15" by 8" for quick access for items such as airway kit, dressings kit, gloves, and blood pressure kit.

Compartment number 9 is a pocket with Velcro secured flap for containment of items such as drugs while 10 is the strap to secure the bag to the metal frame at the uppermost metal support bar. Compartment 11 is 2" by 15" by 24" and comprises of the area between the two front uppermost sections providing additional space for bulky items. 12 and 13 are pictured in FIG. 3 as elastic loops and pocket space for smaller items.

As the pack frame, ring and pin combo, hip belt, shoulder straps buckle, and Velcro are commercially available, they are not described or pictured in FIG. 1 through 4 except for placement purposes. FIG. 1 is a side view—FIG. 2 is front view in a closed position FIG. 3 is a front view in the open position—FIG. 4 is the back view

I claim:

1. An off road rescue backpack adapted to be secured to a metal backpack frame, said backpack comprising:

a substantially rectangular front wall, back compartment defined by a rectangular front wall, back wall, top wall, bottom wall and two side walls, said walls secured along mating edges to define said main compartment;

a first partition wall secured between said side walls and said front and back walls, said first partition wall dividing said main compartment into substantially rectangular-shaped top and bottom compartments and further dividing said front wall into rectangular top and bottom front walls;

said top front wall including a top flap with one edge integral with one of said side walls, said top flap extending substantially between said top wall, said first partition wall and said opposite side wall, closure means secured along the remaining edges of said top flap for releasably securing said top flap to said top front wall;

said top compartment including two parallel adjacent rectangular inner partition walls each having edges secured to said top, back and first partition walls equidistant from a vertical center line of said top compartment, a rectangular front central closure wall secured to and between said inner partition wall edges and extending the length thereof thereby defining a central pocket;

said central closure wall including closure means for accessing the interior of said central pocket, said central pocket adapted to receive a D-size oxygen cylinder;

said top compartment further including two rectangular outer partition walls each secured to said top, back and first partition walls, said outer partition walls being spaced from said inner partition walls thereby defining two narrow pockets;

said top compartment further including two outer pockets each defined by said top, back, first partition, outer partition and side walls, said outer pockets each including an outer closure wall secured to and between the respective side walls and said outer partition walls and extending the length thereof;

said outer closure walls each having closure means for accessing the interior of said outer pockets;

said bottom front wall including a bottom flap having a horizontal edge integral with said bottom wall, said bottom flap extending substantially between said side walls and said first partition wall, closure means secured along the remaining three edges of said bottom flap for releasably securing said bottom flap to said bottom front wall;

said main compartment including a plurality of webbing straps for support and stabilization, said webbing straps arranged such that there are at least four equally spaced straps extending across each of said side walls and secured thereto, each of said sidewall straps having grommets secured at one end thereof for securing said main compartments along said backpack frame;

said webbing straps further arranged such that there are straps extending across said back wall and secured thereto, each of said back wall straps connecting a pair of said side wall straps;

said main compartment further including a center strap adapted to be looped over a top rung of said backpack frame, said center strap having an intermediate segment secured to said back wall along said center line and having means for securing each end together.

* * * * *